United States Patent [19]
Martin

[11] Patent Number: 4,855,061
[45] Date of Patent: Aug. 8, 1989

[54] METHOD AND APPARATUS FOR CONTROLLING THE COAGULANT DOSAGE FOR WATER TREATMENT

[75] Inventor: Arnold D. Martin, Newbrighton, Minn.

[73] Assignee: CPC Engineering Corporation, Sturbridge, Mass.

[21] Appl. No.: 186,309

[22] Filed: Apr. 26, 1988

[51] Int. Cl.$^4$ .............................................. C02F 1/52
[52] U.S. Cl. .................................. 210/709; 210/743; 210/745; 210/746; 210/96.1; 210/101; 210/105; 210/143; 364/500
[58] Field of Search ............... 210/702, 709, 743, 745, 210/746, 96.1, 103, 105, 101, 143; 364/500, 558

[56] References Cited

U.S. PATENT DOCUMENTS

| | | | |
|---|---|---|---|
| 3,594,313 | 7/1971 | Carlson | 210/709 |
| 3,605,775 | 9/1971 | Zaander et al. | 210/745 |
| 3,618,766 | 11/1971 | Morey | 210/96.1 |
| 3,693,797 | 9/1972 | Topol | 210/96.1 |
| 3,731,807 | 5/1973 | Louboutin et al. | 210/96.1 |
| 3,966,603 | 6/1976 | Grant | 210/86 |
| 4,116,832 | 9/1978 | Tardivel | 210/96.1 |
| 4,282,093 | 8/1981 | Haga et al. | 210/709 |
| 4,282,103 | 8/1981 | Fuhr et al. | 210/709 |
| 4,407,719 | 10/1983 | Van Gorp | 210/695 |

FOREIGN PATENT DOCUMENTS 53-130849 11/1978 Japan .................... 210/745
61-4572 2/1986 Japan .................... 210/745

OTHER PUBLICATIONS

"Cost Saving Instrument Improves Water Quality," Water/Engineering & Management Magazine, Dec. 1985.
Gerdes, "Why Streaming Current?," the Clarifier, vol. 86, No. 1, Milton Roy Company.
"Coagulation/Flocculation," Introduction to Water Treatment, vol. 2, 1984, American Water Works Association.

Primary Examiner—Peter Hruskoci
Attorney, Agent, or Firm—Klarquist, Sparkman, Campbell, Leigh & Whinston

[57] ABSTRACT

Apparatus for controlling the coagulant dosage rate includes a charge sensor located adjacent a coagulant pump for measuring the net electrical charge on coagulated water before water treatment and a turbidity meter for measuring the effluent turbidity after water treatment. A programmable controller responds to the output signal of the charge sensor to continuously adjust the dosage rate to maintain a set point of charge value in the coagulated water corresponding to a desired effluent turbidity. To maintain calibration of the charge sensor, the controller is also responsive to the output signal of the turbidity meter to adjust the charge value set point as required so that the it corresponds to a preselected effluent turbidity.

11 Claims, 7 Drawing Sheets

METHOD AND APPARATUS FOR CONTROLLING THE COAGULANT DOSAGE FOR WATER TREATMENT

BACKGROUND OF THE INVENTION

This invention relates to water treatment and, more particularly, to a method and apparatus for controlling the dosage rate of coagulant added to water to maintain a desired turbidity.

The coagulation process is used in water treatment to remove nonsettleable solids, particles otherwise too small to be easily removed by sedimentation or filtration. In coagulation, these nonsettleable solids are converted into larger and heavier settleable solids by adding and mixing chemical coagulants such as alum into the raw water. The settleable solids can then be removed by conventional flocculation, clarification, and filtration processes. Typically, the coagulant is added to the raw water or influent before it enters the main portion of a water treatment plant that includes the above processes.

Prior methods for controlling the coagulant dosage rate have varied. A simple method employed by many water treatment plants is to measure the turbidity of the treated water or effluent and manually adjust in response to the measurement the dosage rate of a coagulant pump dispensing coagulant into the water before it is filtered. More sophisticated methods employ an automatically controlled pump that adjusts the dosage rate based on electrical signals from a turbidity meter. Examples of such prior methods are disclosed in U.S. Pat. Nos. 3,605,775; 3,618,766; 3,693,797; and 3,731,807. U.S. Pat. No. 3,605,775, for example, discloses a method for controlling dosage that uses an influent turbidity meter and an effluent turbidity meter. The influent turbidity meter provides immediate control of the dosage rate. Its measurement signal is continuously compared to the output signal of the effluent turbidity meter for error correction. U.S. Pat. No. 3,693,797 also measures the turbidity of the water before and after material has been added for filtering. The relative values of the measured turbidities are use to control the addition of the material. Similarly, U.S. Pat. No. 3,618,766 discloses a method for controlling the addition of filter aid chemicals to water which relies on simultaneous measurements of turbidity at an intermediate point in the filter and at the final filter effluent. U.S. Pat. No. 3,731,807 discloses the use of multiple vessels each with a predetermined quantity of liquid and reagent and a turbidity meter for determining the optimum proportion of reagent to be added to the liquid. In all of these methods the level of effluent turbidity must be considered because regulatory agencies rely on effluent turbidity as a measure of water quality.

A problem with measuring effluent turbidity to set the coagulant dosage rate is the lag time between the addition of the coagulant dosage to the raw water and the measurement of the resultant turbidity. The relatively long detention time of the water in passing through the treatment plant makes accurate tracking of changes in raw water turbidity difficult. A sudden change in the turbidity of the influent, for example, will not be sensed by the turbidity meter at the output of the water treatment plant until the water has actually undergone treatment, too late to adjust the dosage rate. If the change is brief, then the dosage rate will overcompensate or undercompensate for an additional time.

Several of the methods disclosed in the above-mentioned patents attempt to overcome this problem by measuring the turbidity at other points in the water treatment. However, measuring turbidity after the coagulant dosage is added and mixed but before water treatment is not an accurate measure of the required dosage for a desired effluent turbidity. Turbidity generally does not correlate to the coagulant needed for effective filtration because of differences in particle size.

Because of the lag time between dosage and measurement of its effect on effluent turbidity, plant operators typically overdose the raw water with coagulant as a safety precaution. Not only is this uneconomical, but the overdose can adversely affect the quality of water leaving the water treatment plant. For example, tap water treated with excessive alum contains soluble aluminum which can contribute to serious health problems. Excessive alum can also affect plant operation by reducing filter run times and raising backwash and pumping costs.

Recently devices have been introduced that measure the net ionic and colloidal surface charge of the suspended particles rather than turbidity. This net charge is a function of the balance of free positive and negative charges after coagulation and therefore varies proportionally with the concentration of free particles in a test cell. By measuring the net electrical charge, such devices can accurately detect changes in the concentration of the nonsettleable particles which are affected by the coagulant. And by relying on net electrical charge present after coagulation rather than effluent turbidity after water treatment to control the coagulant dosage, the devices can be located adjacent to the coagulant pump to detect and correct for changes in the influent turbidity immediately. An example of such a device is a streaming current detector available from Milton Roy Company of Ivyland, Pa. In common with many of such charge sensing or measuring devices, the detector has an adjustable gain and zero offset that must be calibrated to the desired level of effluent turbidity with a turbidity meter or other turbidity measuring means. The detector may be combined with a conventional controller to automatically control the dosage rate of a coagulant pump. When used with a controller, the streaming current detector is initialized to a desired net charge value (such as a neutral charge or 0 reading) and the controller is then programmed to maintain that charge value as a set point by adjusting the dosage rate of the coagulant pump. A detected increase in particle concentration produces a positive reading while a decrease in particle concentration prompts a negative reading. The controller responds to the reading to change the dosage rate of the coagulant pump accordingly.

Although these charge measuring devices are a great improvement over earlier methods of dosage control, they have their own drawbacks. For example, they are subject to measurement variation because of fouling of electrodes, amplifier drift, variations in the sample pH, and variations in the sample temperature. Over time, these variations can erroneously change the net charge value measured by the detector and thus cause the controller to adjust the coagulant dosage rate to maintain the set point. The conventional manner of correcting the device is to periodically clean or replace it. Such procedures, however, are costly and require suspension of plant operation.

SUMMARY OF THE INVENTION

An object of the invention, therefore, is to provide method and apparatus for improved water treatment.

Another object of the invention is to provide an improved method and apparatus for controlling the coagulant dosage rate for water treatment.

Another object of the invention is to provide such an apparatus that maintains immediate and accurate control of the coagulant dosage rate by reference to the effluent turbidity.

To achieve these objects, an apparatus according to the invention comprises charge sensing means adjacent to the coagulant pump for sensing the net electrical charge on the raw water immediately after addition of the coagulant and before further water treatment, a turbidity meter for measuring the effluent turbidity after water treatment, and control means responsive to both the charge sensor and turbidity meter. The control means, such as a programmable logic controller or a microprocessor-based controller, responds to the output signal of the charge sensing means to continuously adjust the dosage rate of the coagulant pump to mantain a set point of charge value to be measured by the charge sensing means. This set point is initially calibrated to correspond to a desired effluent turbidity. To maintain the calibration of the charge sensing means as its accuracy varies over time, the control means responds to the output signal of the turbidity meter. The control means determines if the measured effluent turbidity falls within a desired turbidity range and adjusts the set point of charge value accordingly so that the set point continues to correspond to the desired effluent turbidity.

In the present embodiment, the charge sensing means is located at the input of the water treatment plant immediately befor the coagulated water is subjected to flocculation, clarification, and filtration processes within the plant. The turbidity meter is located at the output of the plant to measure the effluent turbidity of the treated water. The charge sensing means may comprise a streaming current detector that produces an output voltage linearly related to the coagulant present in the water to be treated or a zeta meter that applies an electric field across a sample of the water flow to measure particle drift. The turbidity meter is of conventional design.

The foregoing and other objects, features, and advantages of the invention will become more apparent from the following detailed description of a preferred embodiment which proceeds with reference to the accompanying drawings.

DETAILED DESCRIPTION

Figure 1:
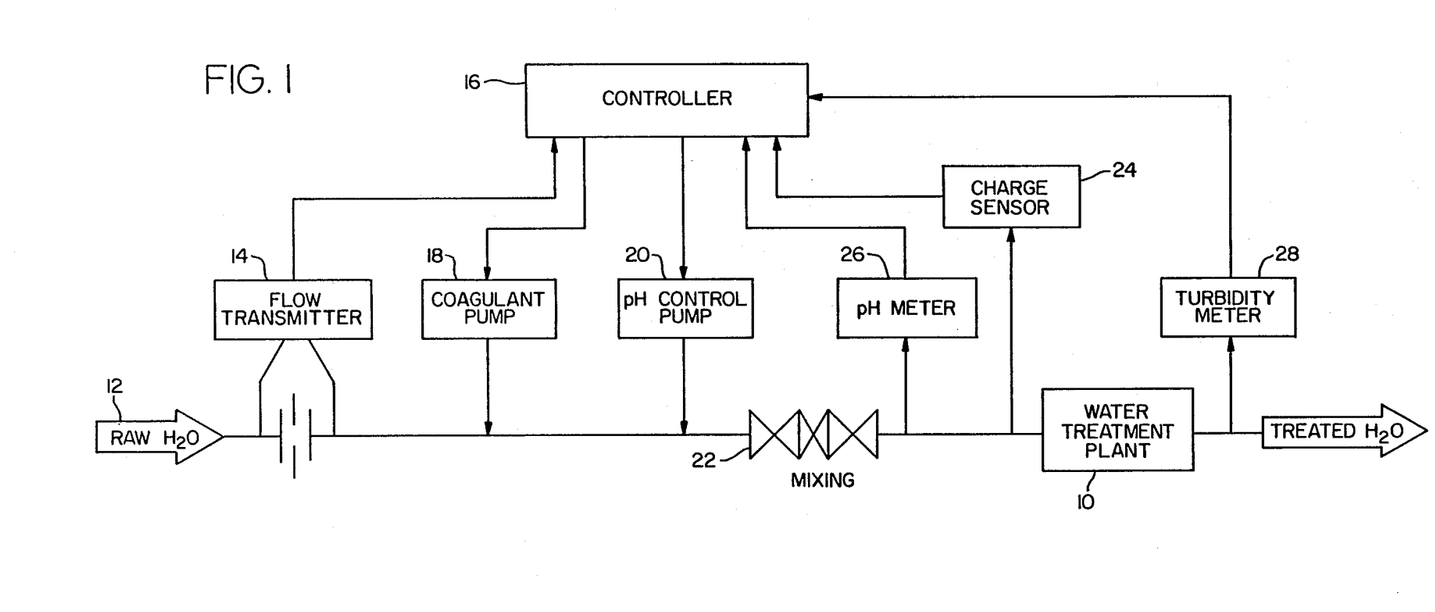
FIG. 1 is a block diagram of the apparatus according to the invention.

Referring now to FIG. 1, a water treatment plant 10 is symbolically shown for receiving influent or raw water 12 at the plant's input. The water treatment plant 10 may be of any type that treats water or other liquids to which a coagulant is added to increase particle size before further treatment of the liquid. Raw water 12 flowing into the plant 10 first passes by a flow transmitter 14. The transmitter 14 is of conventional design such as of the type manufactured by Rosemount Corporation of Minneapolis, Minn., which generates a linear flow signal proportional to the water flow. The flow signal is communicated to control means such as a microprocessor-based controller or a conventional programmable logic controller 16 which can interpret and generate analog signals. At the option of the plant operator, controller 16 is responsive to the flow signal to maintain the dosage rates of a coagulant pump 18 and pH control pump 20 proportional to the rate of water flow. Pump 18 is one form of a means for feeding a coagulant, such as aluminum sulfate or a cationic polymer, into the water to cause coagulation. Similarly, pump 20 is one form of a means for feeding a pH agent to the water to control the pH. Conventional mixing apparatus 22 mixes the water 12 with the added coagulant and pH agent before the water enters the water treatment plant 10. Upon mixing, the coagulant causes nonsettleable particles in the water to coagulate for removal by conventional flocculation, clarification, and filtration processes carried out within the plant 10. The pH agent is added to maintain the water within a desired pH range so that the electrical charge measured in the water 12 relates to particle concentration rather than to the water's pH.

Means such as a charge sensor 24 are provided for measuring the net electrical charge of the coagulated water immediately after addition of the coagulant. The measurement signal is communicated to the controller 16 for adjusting the feed rate of the pump 18 to maintain a set point within the controller of charge value measured by the sensor 24. Such means may comprise a streaming current detector such as is available from the Milton Roy Company of Ivyland, Pennsylvania, or other charge sensor that measures the net ionic and colloidal surface charge (positive and negative) of the particles suspended in the water 12. Such means may also comprise a zeta meter such as is available from Zeta Meter, Inc., of New York, N.Y. In the typical streaming current detector, a piston pulls coagulated water into a cylindrical sampling cell. The temporarily immobilized particles in the cell adhere electrostatically to the cell walls. A back and forth motion of the piston causes counter ions to be stripped from the particles, creating a streaming current measured by electrodes within the cell. Circuitry within the sensor 24 then determines the strength and nature of this current by measuring the relative content of positive and negative ions in the particles. During the reciprocating stroke, the piston creates an alternating current of microamperes. A transconductance amplifier then amplifies the current and converts it into an output voltage. The output voltage, linearly related to the alternating streaming current, is then rectified so that the voltage correlates with the net electrical charge of the particles. This voltage, in the present embodiment, is reconverted to a current signal that is communicated to the controller 16. The sensor 24 must be calibrated to the desired effluent turbidity. The method of doing so in the present invention will be described.

Adjacent to the charge sensor 24 is a conventional pH meter 26 for measuring the pH of the coagulated water. The output signal of the meter 26 is communicated to the controller 16 to adjust the dosage rate of the pH pump 20 to maintain a constant pH in the water 12. A constant pH is required because the charge sensor 24 cannot readily distinguish between a change in the electrical charge due to a change in pH and a change in electrical charge due to a change in concentration of colloidal particles.

Means are also provided for measuring the effluent turbidity at the output of the water treatment plant, after the coagulated water has been subjected to sedimentation and filtration processes to remove particles. Such means may comprise a conventional turbidity meter 28 of a known type which measures the turbidity of a liquid and produces an electrical output signal in response which is proportional to the turbidity measured. Such meters are known in the art, and a typical turbidity meter utilizes a photosensor and a light source arranged so that the liquid to be measured passes between the photosensitive device and the light source. The greater the turbidity, the greater share of the light reflected to the photosensor. This output signal is also communicated to the controller 16 and is used therein to adjust the set point for the charge sensor 24, as will be described. As discussed in the background of the invention, such adjustment becomes necessary to maintain the calibration of sensor 24 in the face of measurement variation.

Figure 2:
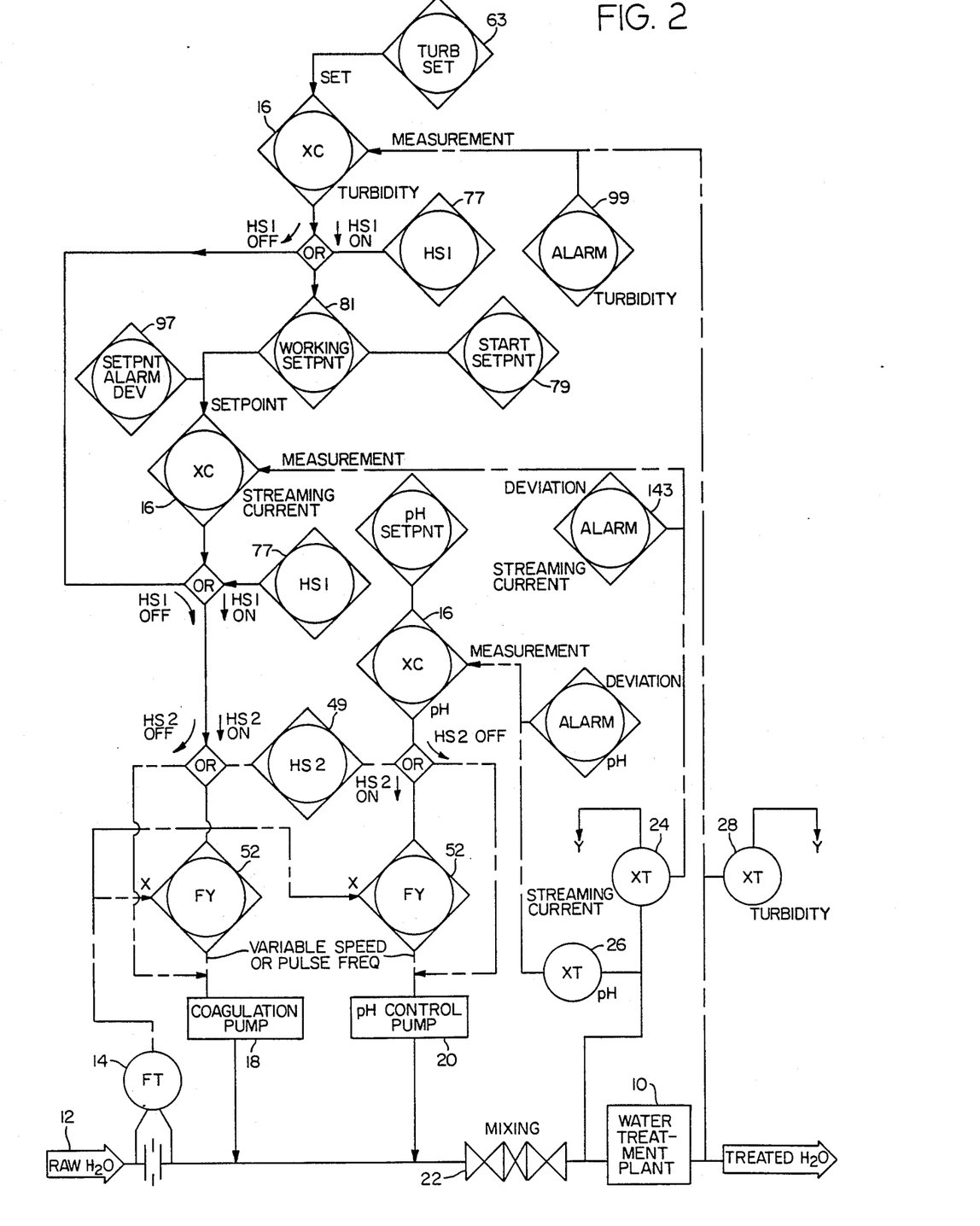
FIG. 2 is a process diagram of the method of the invention.

FIG. 2 is a process diagram showing graphically the operation of the invention, and FIGS. 3A–3F are flowcharts of the controller's operation in FIG. 2. The steps taken by the controller are numbered on the flowcharts and a statement herein describing a step will be followed by the corresponding number in parenthesis. The figures refer to a streaming current detector as the type of charge sensor employed in this embodiment. It should be understood, however, that any type of charge sensor capable of measuring the net electrical charge of the coagulated water could be employed by one skilled in the art.

Figure 3A:
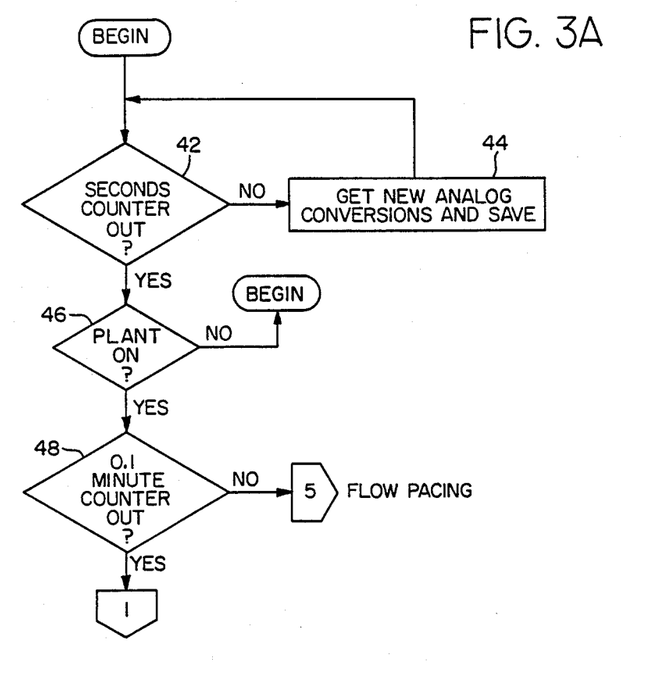
FIGS. 3A-3F are flowcharts showing the relevant operation of the programmable controller shown in FIGS. 1 and 2.

Initially, the sensor 24 is disabled and the controller 16 responds to the output signal of the turbidity meter to set the coagulant dosage rate. Such is a conventional mode of operation and is employed herein for calibrating the sensor 24. This mode may also be employed if the streaming current detector malfunctions and must be turned off for repair or replacement. Referring now to FIG. 3A and with the sensor 24 initially calibrated, the controller 16 monitors a first internal repeating counter (42), reading periodically the analog outputs of the flow transmitter 14 (marked as FT in FIG. 2), charge sensor 24, pH meter 26 and turbidity meter 28 (marked as XTs in FIG. 2). (44). When the first counter counts out, the controller 16 checks to determine if the water treatment plant 10 is on (46) and, if not, repeats its earlier polling of the meters and sensors. With the plant 10 operational (as indicated in FIG. 2), the controller proceeds to monitor a second internal repeating counter (48).

Figure 3B:
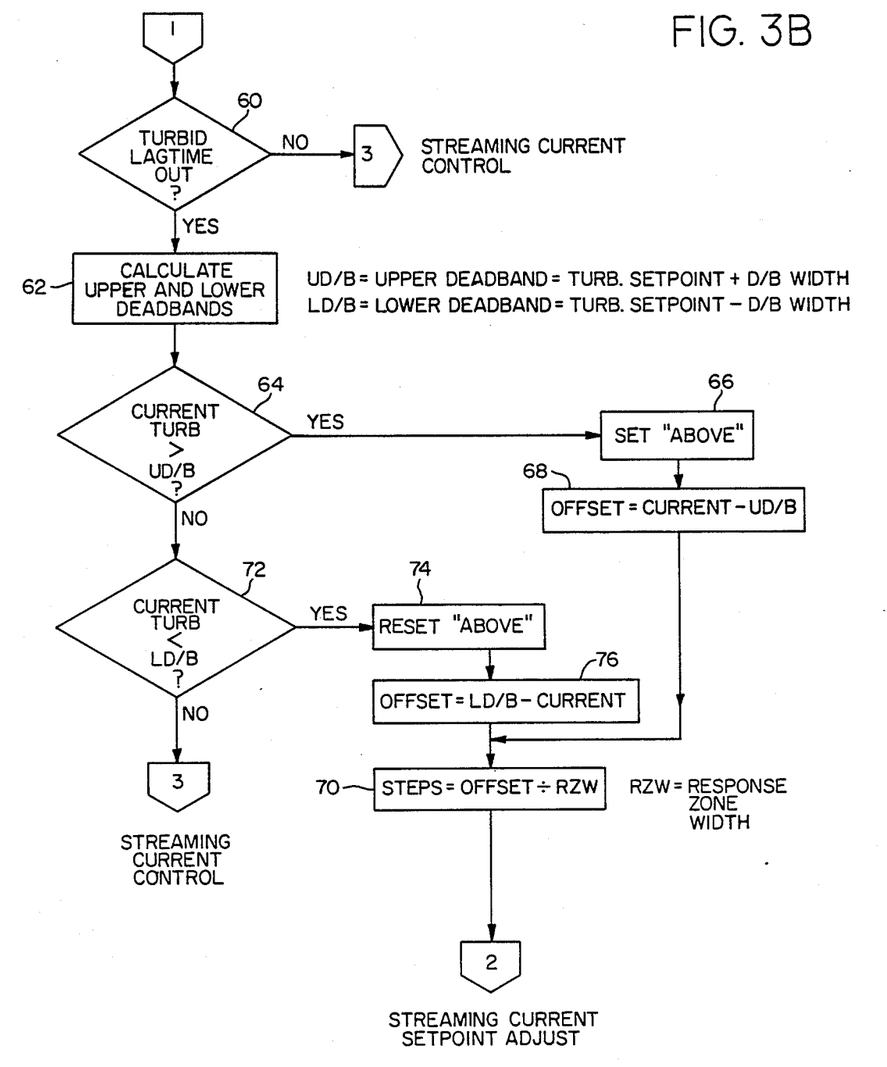
Figure 3C:
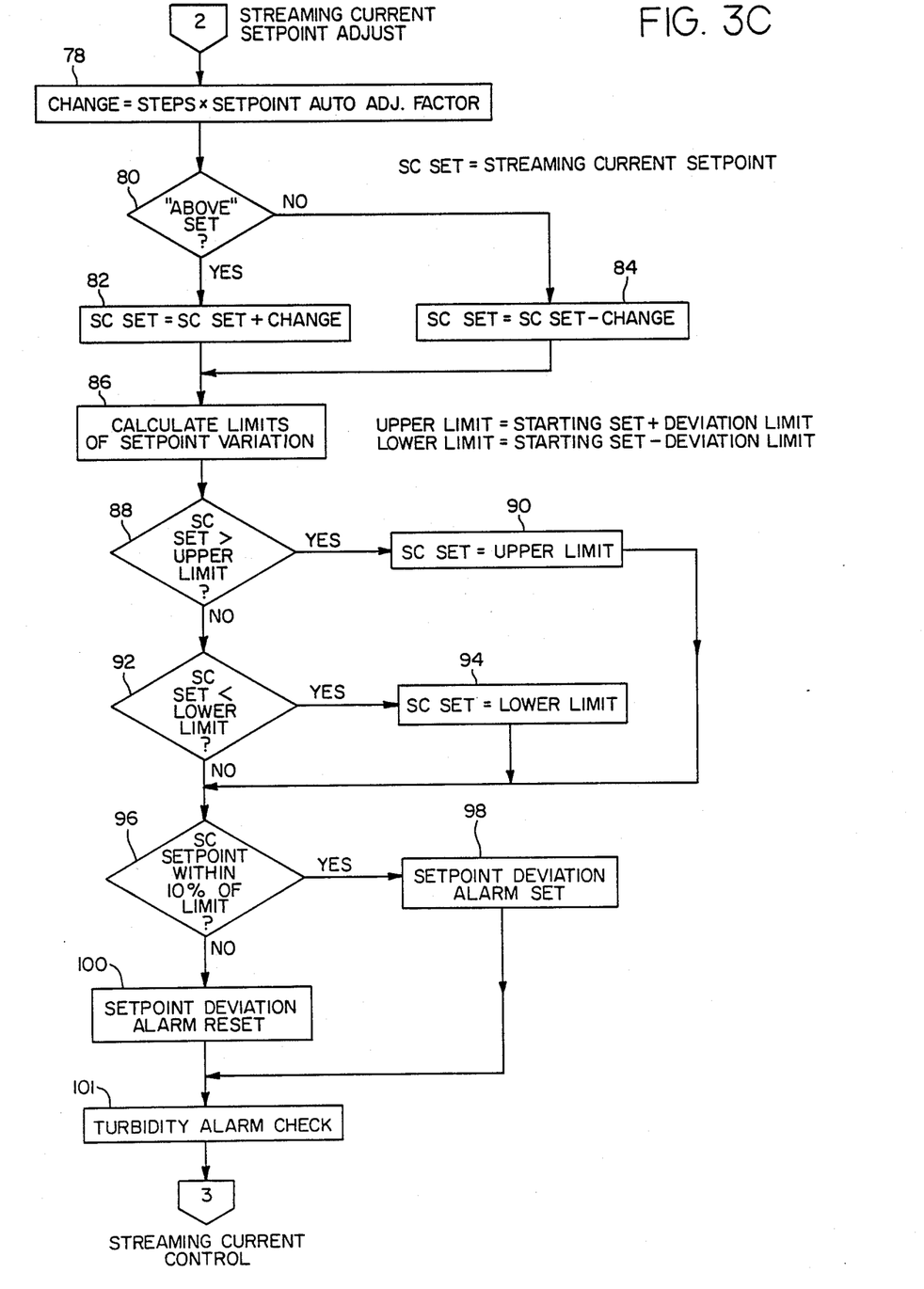
Figure 3D:
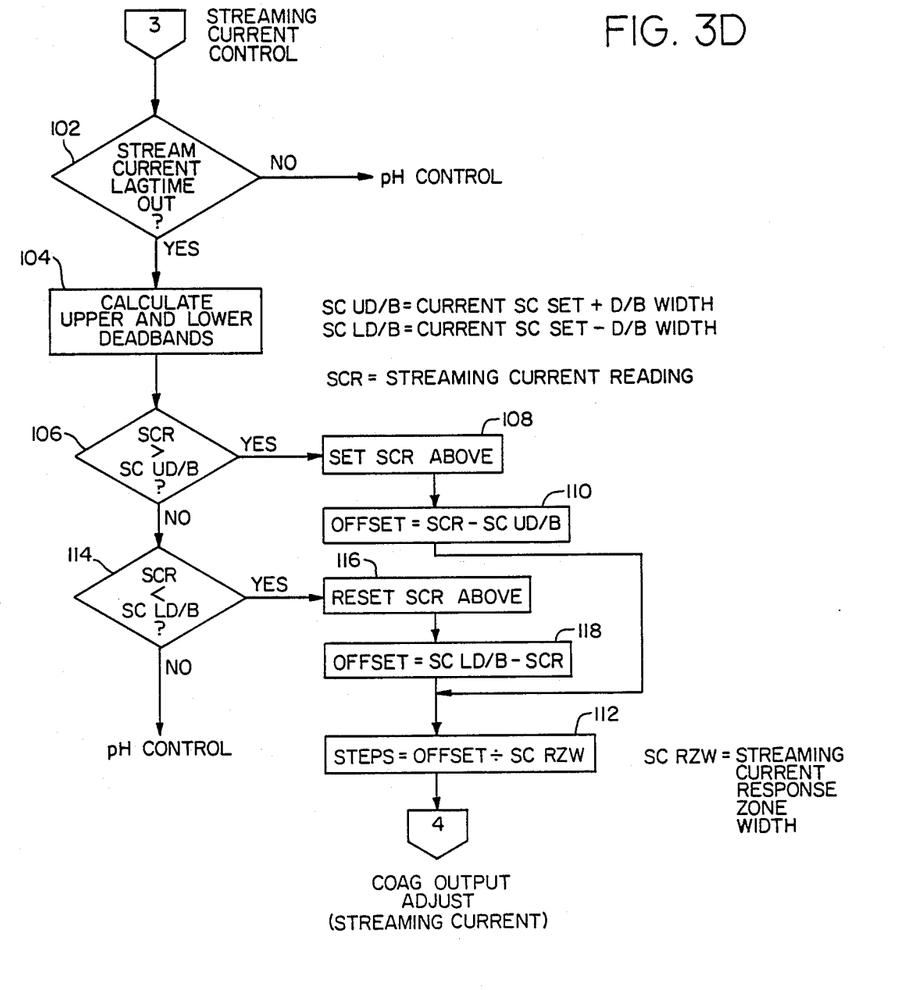
Figure 3E:
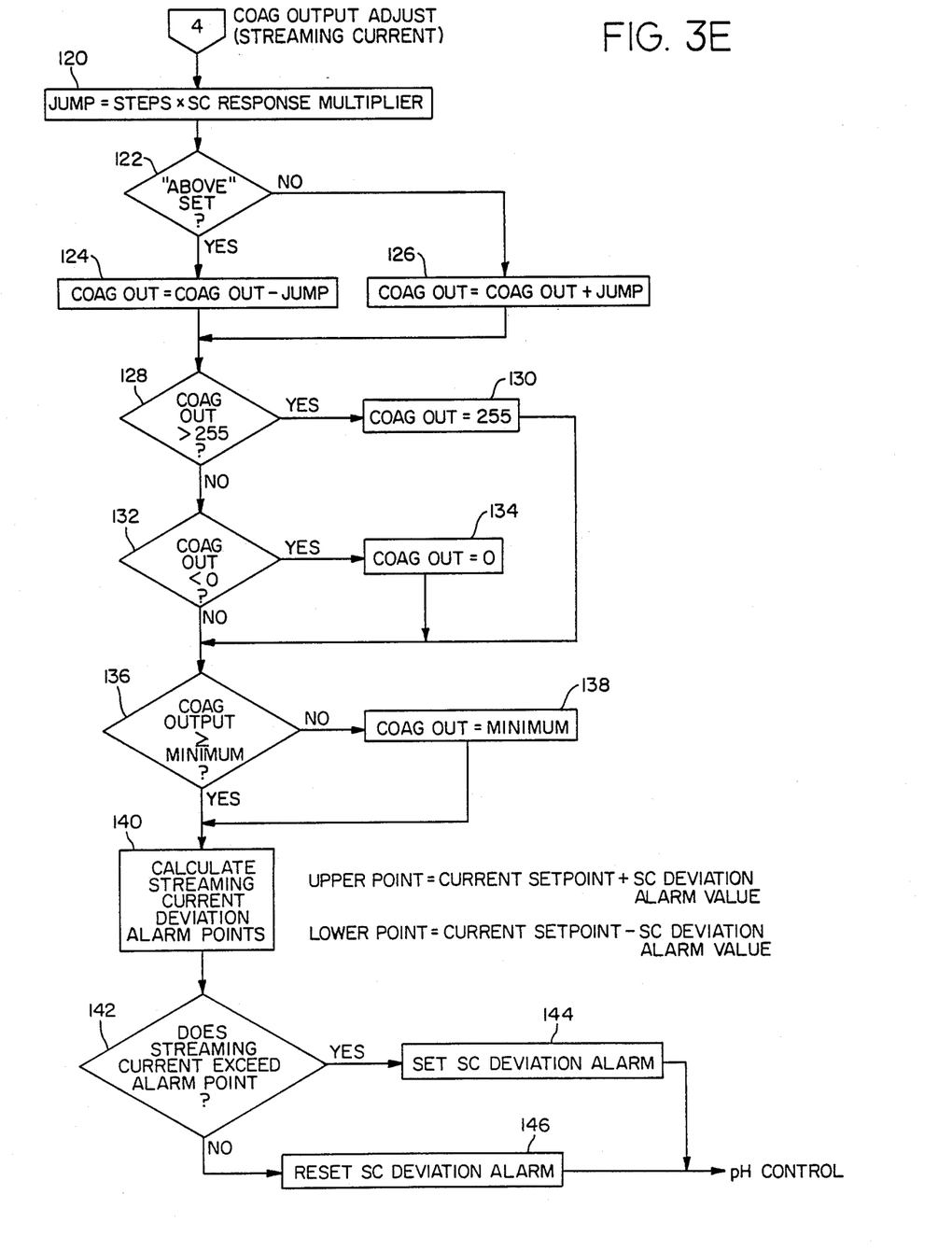
Figure 3F:
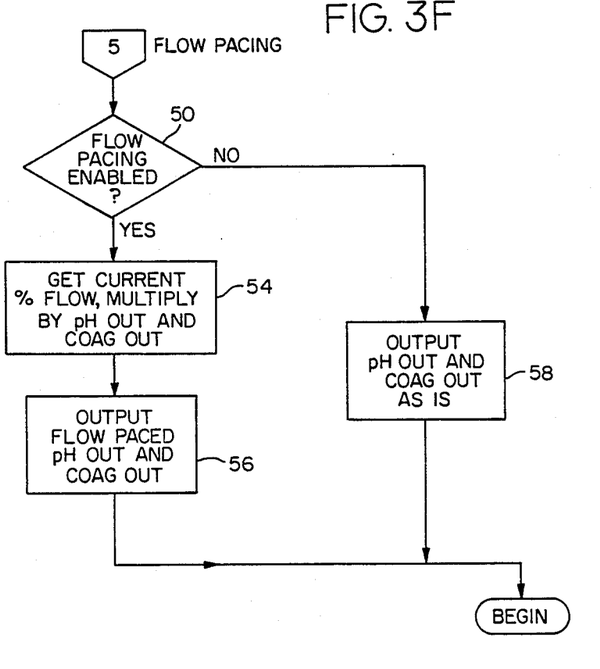

While the second counter is counting toward its target value, the controller checks if the coagulant and pH agent dosage rates are to be adjusted to pace changes in the water flow, as shown in FIG. 3F. Water flow is constant in most water treatment plants, but in some plants the output of treated water is varied. In such plants the flow rate of raw water 12 is automatically regulated to match the output rate, and hence the dosage rates are adjusted to pace the water flow and eliminate the effect of a flow change on the coagulant and pH concentrations. Flow pacing is enabled via a hand switch HS2 (indicated at 49 in FIG. 2) that is controlled by the plant operator (50). As shown in FIG. 2, setting HS2 causes the controller 16 to respond via flow relays 52 to the output of flow transmitter 14. The controller 16 senses the current percentage of the initial rate of water flow and multiplies that percentage times the current coagulant and pH agent dosage rates (54). It then adjusts the dosage rates to pace the water flow (56). If flow pacing is not enabled, the rate of output of coagulant and pH agent are maintained at their current rate (58).

Referring now to FIG. 3B, the controller 16 checks if water treated with a known coagulant dose has reached the turbidity meter 24 (60) each time the second internal counter counts out. The lag time for water treated with the dose to travel through the water treatment plant can range from 20 minutes to several hours, depending on the plant. This lag time is programmed into the controller by the plant operator. Each time the lag time expires, the controller 16 calculates the allowable deadband range of effluent turbidity (62). The deadband limits on this range are determined from a preselected turbidity set point (illustrated in FIG. 2 as turbidity set point 63) plus and minus upper and lower preselected deadband widths. So long as the measured turbidity falls within this range, the controller does not respond to the turbidity output signal. The current turbidity measurement is checked against the upper deadband value (64) and if it exceeds the value, an "above" flag is set within a controller register (66). The controller 16 then calculates an offset of turbidity measurement units from the upper value by subtracting the upper value from the current measurement (68). The offset is then converted into a unitless "steps" value by dividing the offset by a response zone width (RZW) (70), also measured in turbidity units. The RZW is a constant and its value is chosen to scale the size of the offset calculated per lag time. A similar procedure is followed if the current turbidity measurement is less than the lower deadband value (72). In this case, the "above" flag is reset (74) and the offset is calculated by subtracting the current turbidity reading from the lower value (76). The "steps" value is then calculated as before (70).

The controller steps described above and shown in FIG. 3B are taken if the lag time has expired and the current turbidity falls outside the allowable turbidity range. If these conditions are met, then the charge value set point within the controller 16 must be changed to adjust the coagulant dosage rate. In the present invention, the charge value set point is adjusted as will be described and shown in FIG. 3C. However, the operator has the option of disabling the streaming current detector, as previously discussed, by actuating a hand switch HS1, illustrated in FIG. 2 at 77. With HS1 on, the charge value set point is adjustable. With HS1 off, the controller ignores the streaming current detector output and controls the pump 18 solely in response to the output signal of the turbidity meter 28 in a conventional manner. If the current turbidity falls within the allowable range, then the set point is correct and the controller proceeds to monitor the output of the streaming current detector, as will be described and shown in FIG. 3D.

Referring now to FIG. 3C, the steps are shown for adjusting the set point from its initial starting set point (indicated at 81 in FIG. 2). The controller 16 scales the steps (70) to generate a "change" variable by multiplying the "steps" value by a set point adjustment factor (78). The value of the adjustment factor is chosen by the plant operator to regulate the amount of change in the set point per lag time. The amount of change desired is a function of how rapidly the streaming current detector may drift from calibration or how accurately the initial starting set point was chosen. Too large a change in the set point may cause the change to overshoot the desired point while too small a change may cause the change to undershoot the desired point. With the "change" value calculated, the "above" flag is checked (80) to determine the direction of change of the streaming current set point. If the current effluent turbidity is too high, the set point is increased, since the net electrical charge increases as the coagulant increases (82). If the current turbidity is too low, the set point is decreased (84).

The controller then calculates allowable limits to the set point variation (86). These limits are set as a check against possible malfunction of the streaming current detector. The working set point is then checked against the upper limit (88) and if it exceeds that limit, the set point is set at the upper limit (90). The working set point is also checked against the lower limit (92) and if it falls below that limit, the set point is readjusted upward to the lower limit (94). The working set point is then checked to see if it falls within 10% of either limit (96). Such a set point value may indicate a malfunction and causes an alarm to be set and notify the plant operator (indicated at 97 in FIG. 2) and to warn the plant operator (98). If the working set point is not within 10% of either limit, the alarm is reset and does not notify the operator (100). As an additional precaution, a turbidity alarm (indicated at 99 in FIG. 2) is also provided for the controller to notify the plant operator if the effluent turbidity exceeds a desired maximum contaminant level (101).

With the set point checked and adjusted if necessary, the controller 16 proceeds to compare the streaming current detector output reading against the set point. FIG. 3D illustrates the steps for monitoring the detector reading and adjusting changing the dosage rate in response. With the pump 18 responsive to the controller 16, the controller checks if water treated with a known coagulant dose has reached the sensor 24 (102). This lag time through the mixer 22 is typically just a few minutes. After each lag time, the controller 16 calculates the deadband limits of the allowable measurement range. The upper and lower deadband values on this range are determined from the working set point plus and minus upper and lower deadband widths (104). The current detector reading is then checked against this allowable range. If the reading falls within the range, the coagulant rate is considered correct and is not adjusted. If, however, the detector reading is greater than the upper deadband value (106), then an "sc above" flag is set within a controller register (108). An offset is then calculated by subtracting the upper deadband value from the current reading (110), and a "steps" value is calculated by dividing the offset by the streaming current response zone width (SCRZW), similar in purpose to the RZW in FIG. 3B (112). Similarly, if the streaming current reading falls below the lower deadband value (114), the "sc above" flag is reset (116) and the offset calculated by subtracting the current reading from the lower deadband value (118). The "steps" value is then calculated as before (112).

FIG. 3D shows several branches to pH control, at step 102 and step 114. The controller 16 is also programmed to maintain the pH of the water within a preselected range that assures optimum operation of the streaming current detector. Such control is known in the art and comprises monitoring the output signal of pH meter 24 to control the dosage rate of pump 20. In the present embodiment, the control checks the pH after it makes any required adjustments to the coagulant dosage rate or during lag times.

FIG. 3E illustrates the steps for adjusting the coagulant dosage rate. The controller 16 first calculates a "jump" value by scaling the steps by a response multiplier (120). This response multiplier serves the same function as the set point auto adjustment factor to track the rate of turbidity change with large or small jump in the coagulant dosage rate. The controller then checks the setting of the "sc above" flag (122). If the flag is set, the detector reading is too high, indicating an overfeed, and the coagulant output is adjusted downward by subtracting the jump from the current output rate (124). If the flag is not set, the detector reading is too low, indicating an underfeed, and the coagulant rate is adjusted upward by adding the jump to the current dosage rate (126). The adjusted coagulant output rate is then checked to determine if it exceeds a maximum output rate (128) and, if so, the rate is reduced to the maximum (130). The rate is also checked to see if it meets a minimum allowable rate (zero in the present embodiment) (132) and, if not, the rate is adjusted upward to the minimum (134). For low turbidity waters, the controller may be programmed to assure a minimum coagulant dosage rate to remove such contaminants as giardia lamblia cysts (136, 138).

The controller 16 is also programmed to check if the current detector reading is outside an allowable preselected range. Such deviation may indicate a malfunction in the detector such as extreme amplifier drift, fouling of electrodes, or improper initial adjustment of the detector. The controller thus calculates allowable deviation limits from the current set point (140). If the current detector reading exceeds an alarm point (142) (indicated at 143 in FIG. 2), an alarm is set to notify the operator (144). If the detector reading is within the allowable range, the alarm is reset (146).

Having illustrated and described the principles of the invention in a preferred embodiment, it should be apparent to those skilled in the art that the invention can be modified in arrangement and detail without departing from such principles. I claim all modifications coming within the spirit and scope of the following claims.

I claim:

1. In a water treatment system including a means for feeding coagulant into water to be treated to form coagulated particles, apparatus for controlling the coagulant dosage comprising:

charge sensing means for measuring the net electrical charge of the water after addition of the coagulant;
turbidity sensing means for measuring effluent water turbidity after water treatment to remove said coagulated particles and form said effluent water; and
control means responsive to the charge sensing means and the turbidity sensing means for controlling the dosage rate of the coagulant feeding means, the control means responsive to the charge sensing means for adjusting the dosage rate of the coagulant feeding means to maintain a set point of charge value to be measured by the charge sensing means and responsive to the turbidity sensing means for adjusting the charge value set point to maintain a preselected turbidity to be measured by the turbidity sensing means.

2. The apparatus of claim 1 in which the charge sensing means is arranged to measure the net electrical charge of the water after coagulant additions and before water treatment.

3. The apparatus of claim 1 in which the charge sensing means comprises a streaming current detector.

4. The apparatus of claim 1 in which charge sensing means comprises a zeta meter.

5. The apparatus of claim 1 in which the control means comprises a programmable logic controller.

6. The apparatus of claim 1 comprises a microprocessor-based controller.

7. The apparatus of claim 1 including flow proportioning means for maintaining a constant proportion of coagulant dosage to water flow.

8. The apparatus of claim 1 including means for controlling the pH of the water to be treated to maintain a substantially constant pH.

9. Apparatus for controlling the coagulant dosage added to water flowing in a water treatment system comprising:
   means for feeding coagulant into water to be treated to form coagulated particles;
   charge sensing means for measuring the net electrical charge of the water after addition of the coagulant;
   turbidity sensing means for measuring effluent water turbidity after water treatment to remove said coagulated particles and form said effluent water; and
   control means responsive to the charge sensing means and the turbidity sensing means for controlling the dosage rate of the coagulant feeding means, the control means responsive to the charge sensing means for adjusting the feed rate of the coagulant feeding means to maintain a set point of charge value to be measured by the charge sensing means and responsive to the turbidity sensing means for adjusting the charge value set point to maintain a preselected turbidity to be measured by the turbidity sensing means.

10. Apparatus for controlling the coagulant dosage added to water flowing in a water treatment system, comprising:
    a coagulant pump having an adjustable feed rate for feeding coagulant into water to be treated to form coagulated particles;
    a streaming current detector for measuring the net electrical charge of the water after addition of the coagulant and before water treatment to remove coagulated particles and form effluent water;
    turbidity sensing means for measuring the turbidity of said effluent water after said water treatment; and
    a programmable controller responsive to the streaming current detector and the turbidity sensing means for controlling the dosage rate of the coagulant pump, the controller responsive to the detector for adjusting the feed rate of the coagulant pump to maintain a set point of charge value to be measured by the detector and responsive to the turbidity sensing means for adjusting the charge value set point to maintain a preselected turbidity to be measured by the turbidity sensing means.

11. A method of controlling the coagulant dosage added to water flowing in a water treatment system to form coagulated particles comprising:
    measuring the net electrical charge of the water after addition of the coagulant and before water treatment to remove said coagulated particles and form effluent water;
    measuring the turbidity of said effluent water after said water treatment; and
    controlling the dosage rate of the coagulant added to the water in response to measurement of the net electrical charge to maintain a set point of charge value in said water and adjusting the charge value set point in response to measurement of the effluent water turbidity to maintain a preselected turbidity in said effluent water.

* * * * *